United States Patent [19]

Oxman et al.

[11] Patent Number: 5,066,231
[45] Date of Patent: Nov. 19, 1991

[54] DENTAL IMPRESSION PROCESS USING POLYCAPROLACTONE MOLDING COMPOSITION

[75] Inventors: Joel D. Oxman, Minneapolis; F. Andrew Ubel, III, St. Paul, both of Minn.

[73] Assignee: Minnesota Mining and Manufacturing Company, St. Paul, Minn.

[21] Appl. No.: 484,692

[22] Filed: Feb. 23, 1990

[51] Int. Cl.$^5$ .................................................. A61C 9/00
[52] U.S. Cl. ...................................... 433/214; 433/48; 433/71
[58] Field of Search ................ 433/48, 41, 37, 71, 433/214

[56] References Cited

U.S. PATENT DOCUMENTS

| | | | |
|---|---|---|---|
| 3,427,161 | 2/1969 | Laridon et al. | 96/35.1 |
| 3,756,827 | 9/1973 | Chang et al. | 96/86 |
| 3,759,807 | 9/1973 | Osborn et al. | 204/159.23 |
| 4,071,424 | 1/1978 | Dart et al. | 204/159.15 |
| 4,642,126 | 2/1987 | Zador et al. | 51/295 |
| 4,659,786 | 4/1987 | Kawakami et al. | 525/415 |
| 4,828,583 | 5/1989 | Oxman et al. | 51/295 |
| 4,835,203 | 5/1989 | Sieverding | 524/277 |

FOREIGN PATENT DOCUMENTS

| | | |
|---|---|---|
| 150952 | 8/1985 | European Pat. Off. . |
| 63-171554 | 7/1988 | Japan . |
| 63-270759 | 11/1988 | Japan . |
| 1304112 | 1/1973 | United Kingdom . |

OTHER PUBLICATIONS

Tone ® P-300 and P-700 High Molecular Weight Caprolactone Polymers (1988 Product Literature of Union Carbide Corp.).
Chem. Abs. 95:225704U.
Aqueron TM Bite Registration Sticks and Custom Tray Material (Cover Letter Dated Dec. 8, 1989 from E. M. Natt Ltd. with Brochure from Erkodent Company).

Primary Examiner—John J. Wilson
Attorney, Agent, or Firm—Gary L. Griswold; Walter N. Kirn; David R. Cleveland

[57] ABSTRACT

Thermoplastic molding compositions are made from a blend of high molecular weight and low molecular weight polycaprolactones. The blends have lower viscosity, and can have higher modulus, than a composition containing only high molecular weight polycaprolactone. The blends are especially useful for dental impressioning.

7 Claims, 3 Drawing Sheets

DENTAL IMPRESSION PROCESS USING POLYCAPROLACTONE MOLDING COMPOSITION

FIELD OF THE INVENTION

This invention relates to thermoplastic molding compositions. It also relates to dental impression-taking, to the manufacture of dentures, crowns, bridges and other oral prosthetic devices, and to general-purpose modelmaking.

BACKGROUND OF THE INVENTION

High molecular weight poly (epsilon-caprolactone) (also known as "polycaprolactone") has been used as a thermoplastic moldirg compound for general-purpose modelmaking and dentistry. References describing polycaprolactone molding compositions include U.S. Pat. No. 4,835,203, Kokai (Japanese Published Pat. Appl.) Nos. 63-171554 and 63-270759, and TONE® POLYMERS P-300 AND P-700 High Molecular Weight Caprolactone Polymers (1988 product literature of Union Carbide Corp.).

SUMMARY OF THE INVENTION

When the above-mentioned references refer to thermoplastic polycaprolactone molding compositions, they disclose compositions containing only a single grade of high molecular weight polycaprolactone, such as "TONE P-700" or "TONE P-767" 40,000 molecular weight polycaprolactone (Union Carbide Corp.). Hard tooth tissue impressions can be made using warmed high molecular weight polycaprolactone. However, the warm state viscosity is sufficiently high that soft tissue can be distorted and thus improperly modeled. The relatively viscous nature of warm high molecular weight polycaprolactone can also contribute to poor centric occlusion measurements in bite registration impressions. Lower molecular weight polycaprolactones lack rigidity in the cooled state, and may even be liquids at oral temperature. Insufficient rigidity can lead to a distorted impression and eventual poor fit of a denture, crown, bridge, or other prosthesis made from the impression.

The present invention provides a polycaprolactone molding composition, useful for dental impressioning and general-purpose modelmaking, comprising a blend of high molecular weight and low molecular weight polycaprolactones, the blend being solid at 38° C., and having a melting or softening point that comfortably can be withstood by oral tissues.

The invention also provides a method for making an impression of dental tissue, comprising the step of enveloping the tissue with a molten or softened molding composition comprising a blend of high molecular weight and low molecular weight polycaprolactones.

The molding compositions of the invention have low viscosity in the warm state and good rigidity in the cool state, thus facilitating the making of improved impressions and models, especially when soft tissues and other pliable substances are modeled.

DETAILED DESCRIPTION

Figure 1:
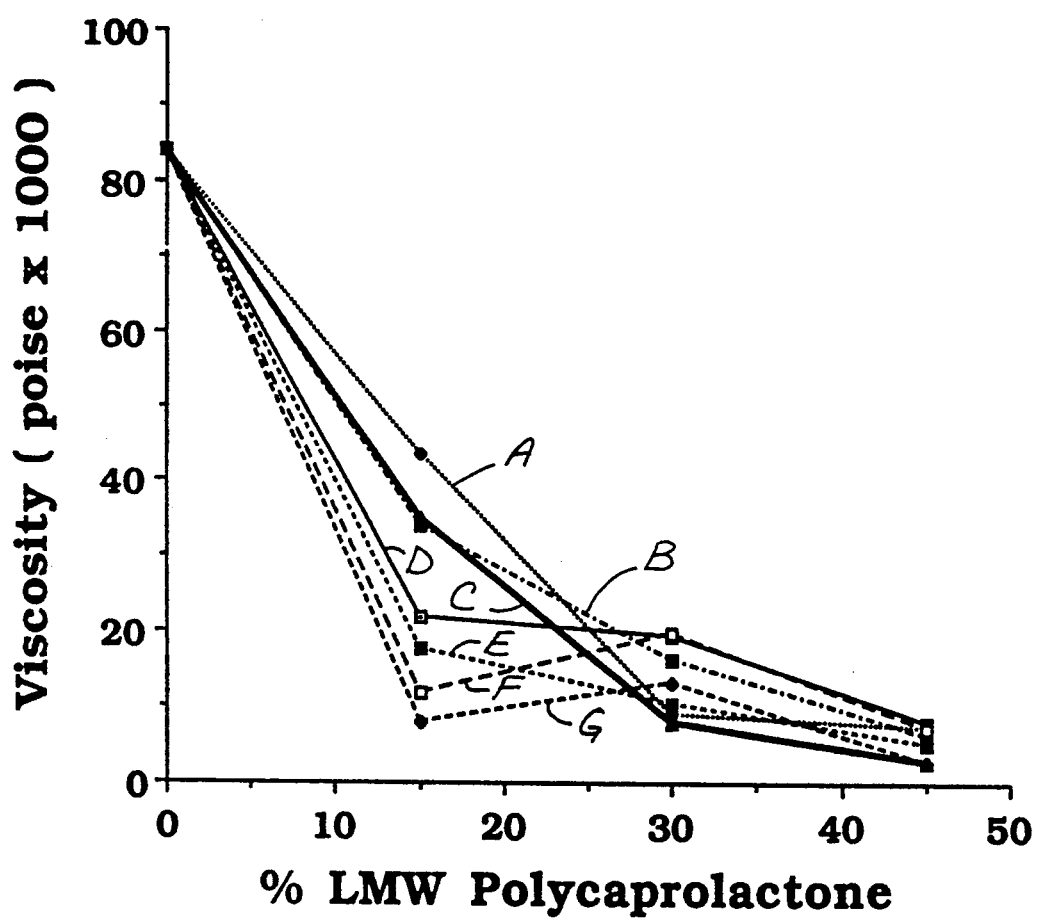
FIG. 1 is a plot of viscosity vs. percent low molecular weight polycaprolactone for the compositions of Runs 1-22 of EXAMPLE 1.

For brevity, the term "molecular weight" in this specification refers to "weight average molecular weight". Although molecular weight can be determined in a variety of ways, with some differences in result depending upon the method employed, it is convenient to employ solution viscometry, or low angle laser light scattering with trifluoroethanol as the solvent. Standard sample isolation and preparation techniques should be observed The molding compositions of the invention contain both high molecular weight and low molecular weight polycaprolactone. The terms "high" and "low" are of course relative, but as used in this specification "high molecular weight polycaprolactone" refers to an epsilon-caprolactone homopolymer or copolymer whose molecular weight is as great as or greater than the lowest molecular weight substantially neat epsilon-caprolactone homopolymer heretofore used commercially for dental impressioning purposes. Thus, the high molecular weight polycaprolactones that can be used in the invention are believed to have a molecular weight of at least about 20,000, and preferably at least about 30,000.

The high molecular weight polycaprolactones preferably have the following formula:

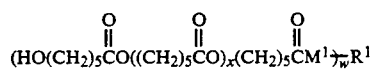

$$(HO(CH_2)_5CO((CH_2)_5CO)_x(CH_2)_5CM^1)_w R^1 \qquad \text{I.}$$

where $R^1$ is hydrogen or an aromatic or a straight chain or branched aliphatic backbone, which can optionally contain one or more non-interfering substituents such as hydroxyl or amine groups, w is 1 if $R^1$ is hydrogen, and w otherwise has an average value of about 1 to about 4, $M^1$ is oxygen or $-NR^2-$ where $R^2$ is hydrogen or a non-interfering aromatic or aliphatic group, and the product of w times x is greater than about 175. The product of w times x is preferably at least about 250 and more preferably between about 250 and about 440.

The low molecular weight polycaprolactone is an epsilon-caprolactone homopolymer or copolymer whose molecular weight is less than the molecular weight of substantially neat epsilon-caprolactone homopolymer heretofore used commercially for dental impressioning purposes. Thus, the low molecular weight polycaprolactones that can be used in the invention are believed to have a molecular weight less than about 20,000, and preferably less than about 10,000. The low molecular weight polycaprolactones preferably have the formula:

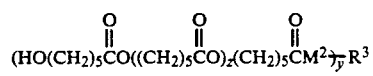

$$(HO(CH_2)_5CO((CH_2)_5CO)_x(CH_2)_5CM^2)_y R^3 \qquad \text{II.}$$

where $R^3$ is hydrogen or an aromatic or a straight chain or branched aliphatic backbone, which can optionally contain one or more non-interfering substituents such as hydroxyl or amine groups, y is 1 if $R^3$ is hydrogen and y otherwise has an average value of about 1 to about 4, $M^2$ is oxygen or $-NR^4-$ where $R^4$ is hydrogen or a non-interfering aromatic or aliphatic group, and the product of y times z is less than about 175. The product of y times z is preferably less than about 100, and more preferably is between about 3 and about 90.

As a further guide, the molecular weight ratio of high to low weight polycaprolactones preferably is between about 9:1 to 1:9, and will depend in part on the intended use for the composition.

The polycaprolactone can contain property-modifying or cross-linkable functional groups (for example, hydroxyl, acrylate, methacrylate, epoxy, isocyanato, or vinyl groups) if desired. Preferred commercially available high molecular weight polycaprolactone polymers include the above-mentioned "TONE P-700" and "TONE P-767" polycaprolactones, the "CAPA" polycaprolactones "630" (30,000 molecular weight), "640" (40,000 molecular weight), "650" (50,000 molecular weight) and "656" (56,000 molecular weight) from Interox, and the various high molecular weight polycaprolactones available from Daicell Chemical Industry Co., Ltd. Preferred commercially available low molecular weight polycaprolactone polymers include "TONE P-:00" polycaprolactone (10,000 molecular weight), the "TONE" polycaprolactone diols "0200" (530 molecular weight), "0210" (830 molecular weight), "0230" (1,250 molecular weight), "0240" and "2240" (2,000 molecular weight), and "0250" (3,000 molecular weight), "TONE" polycaprolactone triols "0301" (300 molecular weight), "0305" (540 molecular weight) and "0310" (900 molecular weight) from Union Carbide Corp., as well as the "CAPA" polycaprolactone diols "203" (400 molecular weight) through "240" (4,000 molecular weight), "CAPA" polycaprolactone triols "304" (250 molecular weight) and "305" (540 molecular weight), and the "CAPA" polycaprolactone tetraol "316" (1,000 molecular weight) available from Interox.

A preferred embodiment of our invention contains a free-radically polymerizable resin and an initiator, as described in our copending application Ser. No. 07/484,695 the disclosure of which is incorporated in this specification by reference. Suitable free-radically polymerizable resins contain at least one ethylenically unsaturated monomer, oligomer, or polymer capable of undergoing addition polymerization. Such monomers include mono-, di- or polyfunctional acrylates and methacrylates such as methyl acrylate, methyl methacrylate, ethyl acrylate, isopropyl methacrylate, n-hexyl acrylate, styryl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,3-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, tris-hydroxyethylisocyanurate triacrylate, beta-methacrylaminoethyl methacrylate, and mixtures thereof. Other suitable monomers include unsaturated amides such as methylene bisacrylamide, methylene bis-methacrylamide, 1,6-hexamethylene bis-acrylamide and diethylenetriamine trisacrylamide. Suitable oligomeric or polymeric resins include 200 to 500 molecular weight polyalkylene glycols, acrylated or methacrylated oligomers such as those of U.S. Pat. No. 4,642,126, acrylated urethanes such as "SARTOMER" 9503, 9504 and 9505 (Sartomer Corp.), "INTEREZ" CMD 8803, 8804 and 8805 (Radcure Specialties, Inc.), and "PHOTOMER" 6060, 6110, and 6160 (Henkel Corp.), as well as acrylated polyester oligomers such as "EBECRYL" 830 (Radcure Specialties, Inc.). Mixtures of free-radically polymerizable monomers, oligomers or polymers can be used if desired.

The free-radically polymerizable resin can if desired be cured using a conventional chemical initiator system, such as a combination of a peroxide and an amine. However, chemical cure systems typically require at least partial ingredient separation before use. The resin is preferably cured using a photoinitiator, optionally combined with a suitable photosensitizer or accelerator. The photoinitiator should be capable of absorbing actinic radiation and generating free radicals for addition polymerization, at some wavelength between 200 and 800 nm. Suitable photoinitiators include alpha-diketones, monoketals of alpha-diketones or ketoaldehydes, acyloins and their corresponding ethers, chromophore-substituted halomethyl-s-triazines, chromophore-substituted halomethyl-oxadiazoles, aryliodonium salts, and other commercially available ultraviolet ("UV") and visible light photoinitiators. Preferred photoinitiator systems include a mono or diketone photoinitiator together with a suitable donor compound or accelerator, such as the systems described in U.S. Pat. Nos. 3,427,161, 3,756,827, 3,759,807, 4,071,424, 4,828,583, U.K. Pat. Specification No. 1,304,112, European Published Pat. Appl. No. 150,952 and Chem. Abs. 95:225704U.

The molding compositions of the invention can contain a wide variety of adjuvants depending upon the desired end use. Suitable adjuvants include solvents, diluents, plasticizers, pigments, dyes, inorganic or organic fibrous or particulate reinforcing or extending fillers, thixotropic agents, indicators, inhibitors, stabilizers, UV absorbers, medicaments (e.g., leachable fluorides), biocides and the like. For custom tray applications, the molding composition preferably contains one or more fillers that limit the composition's 60° C. relaxation stress at equilibrium, as, described in our copending application Serial No. 07/484,106, the disclosure of which is incorporated in this specification by reference.

The amounts of high molecular weight and low molecular weight polycaprolactone, and the amounts of other ingredients in the molding compositions of the invention, usually will be empirically selected. Selection should be based in part on the desired end use for the composition and the desired properties in the molten or softened ("warm") and solid ("cool") states. The warm state is characterized by an amorphous polycaprolactone microstructure, and by appreciable mass flow under moderate (hand) pressure at some temperature between body temperature (about 38° C.) and the maximum temperature that comfortably can be withstood by oral tissues. This maximum temperature is generally thought to be about 75° C., although a maximum of about 65° C. is preferred. The cool state is characterized by a semi-crystalline polycaprolactone microstructure, and by minimal apparent mass flow under moderate pressure at temperatures below 38° C.

The warm and cool state properties permit the molding composition to be heated to a moderate temperature, manually shaped in the mouth while warm to conform to adjacent hard and soft oral tissue, and cooled within the mouth to form a substantially rigid model.

The composition should remain substantially homogeneous (that is, it should not undergo mamacroscopic phase separation or filler sedimentation) and preferably should retain its desired properties even if repeatedly cycled between the warm and cool states. Thus the selection of ingredients can be guided in part by the desire to preserve homogeneity and thermoplastic reversibility.

We have found that compositions containing a blend of high and low molecular weight polycaprolactones can have both a higher modulus and a lower viscosity than a composition containing only one of the constituent polycaprolactones. In other words, the blend provides a synergistic combination of modulus and low viscosity. For dental impressioning, the relative amounts of high molecular weight and low molecular weight polycaprolactone are preferably selected so as to provide this synergistic combination. In general, to attain such synergism the majority (by weight) of the pclycaprolactone in the composition should be of the high molecular weight variety. For general-purpose modeling applications (where the solidified model may be subjected to less severe stresses than in dental impressioning), a synergistic increase in modulus may not be desired. Accordingly, somewhat lesser or greater quantities of low molecular weight polycaprolactone can be employed.

As a further guide, the preferred amounts of high and low molecular weight polycaprolactones, filler, polymerizable resin, and photoinitiator for dental impressioning are as follows:

| Ingredient | Preferred Weight % |
|---|---|
| High molecular weight polycaprolactone | 10–90 |
| Low molecular weight polycaprolactone | 10–90 |
| Filler | 0–70 |
| Polymerizable resin | 0–50 |
| Photoinitiator | 0–10 |

The ingredients in the molding composition can be blended by hand or by mechanical mixing. The ingredients preferably are warmed sufficiently to melt the polycaprolactones, but if desired can be mixed at lower temperatures. Any suitable mixing device can be used, including kettles equipped with a mechanical stirrer, extruders, rubber mills, and the like.

The molding composition can be put up in a variety of forms including preformed sheets, arch-shaped trays, ropes, buttons, woven or non-woven webs and the like. The composition can be shaped in a variety of ways including extrusion, injection molding and web processing using a coating knife or rollers. The composition can be sold unwrapped, loosely wrapped in a package, or packaged in tubes, syringes, flexible outer plastic skins, plastic or metal trays and the like. The composition can be extruded or cast in mono-, bi, or poly-layers (for example, coplanar layers or layers arranged in core-shell fashion) in which each layer has a selected melting temperature, viscosity, modulus, stickiness, or other desired physical properties.

The molding composition can be converted from the cool state to the warm state by using a variety of energy sources. The composition can be immersed in a heated bath containing a suitable inert liquid (for example, water or a fluorochemical fluid) that will not dissolve or swell the composition in either its cool or warm states. The composition can also be softened using heat sources such as a hot air gun, hot plate, conventional oven, infrared heater, or microwave oven. The composition can be encased in a plastic pouch, syringe or other container which is in turn heated (e.g. electrically), or subjected to one or more of the above-mentioned heating methods.

Transforming the molding composition from a warm state to a cool state requires loss of thermal energy and can be carried out using a variety of cooling techniques. Cooling can take place under ambient conditions in the presence of air only. Cooling can be expedited using forced air, cold water, ice, or heat sinks such as chilled "cold packs" or flexible pouches containing low boiling inert liquids. Of particular interest for both dental and orthopedic applications are chilled cold packs in flexible pouches that have been preshaped to match the contours of the model being cooled For example, flexible pouches containing a chilled coolant can be fabricated in the shape of a full arch or quadrant and placed intraorally in contact with the warm molding composition. Analogously, a large coolant-filled blanket can be draped around an orthopedic casting or splint material prepared from a molding composition of the invention.

A simplified dental impression system can be prepared from the molding composition. Traditional impressioning systems employ one or more low viscosity flowable elastomeric materials such as an alginate, hydrocolloid, polyvinylsiloxane, polyether, or polysulfide contained in a fairly rigid adhesive-coated plastic or metal arch-shaped tray. The elastomeric material often is applied both to the dental tissue to be modeled and to the tray. The elastomeric material and surrounding tray are subsequently pressed against the dental tissue, and left in place until the elastomeric material has hardened. This traditional process involves several materials and steps, material waste and fairly lengthy set times.

The present invention permits impressioning using a monolayer or a bilayer thermoplastic molding composition. The monolayer model, or at least one layer of the bilayer model, is made from a molding composition of the invention. In a preferred embodiment, a flat sheet or a preformed arch-shaped tray is made from two coextruded thermoplastic layers. The physical properties of each layer emulate in part the properties of a conventional rigid tray and the elastomeric material respectively. At a suitable elevated temperature the "tray" layer becomes a conformable, non-sticky melt (thereby permitting the warm tray layer to be hand shaped into a custom tray configuration) and the "elastomer" layer exhibits good flow and low viscosity (thereby permitting the warm elastomer layer to flow around tooth tructure and provide an accurate model). The warm bilayer construction provides easy placement, accurate impressioning, and efficient use of materials. Cooling can take place rapidly, and in less time than is required to harden a conventional impression. Once cooled, the tray layer exhibits sufficient rigidity to discourage distortion of the impression during removal from the mouth or during subsequent handling. The elastomer layer provides stable, accurate modeling of hard and soft dental tissue.

If desired, a custom impression tray can be formed from a molding composition of the invention and filled with a conventional elastomeric impression material (for example, a silicone elastomer). By shaping the tray in the mouth before (or if desired, after) it is filled with elastomer, the tray volume and required amount of elastomer will be minimized.

The molding compositions of the invention have many other uses. For example, they can be used to prepare crowns, bridges, dentures, splints and pontics. They can also be used to prepare shapeable orthopedic casts and splints. They can be used in modelmaking, for example in tool and die-making. They will find general use in applications requiring rapid, accurate shaped object formation.

The following examples are offered to aid in understanding the invention and are not to be construed as limiting its scope. Unless otherwise indicated, all parts and percentages are by weight.

EXAMPLE 1

85 Parts "TONE P-767" (40,000 molecular weight) polycaprolactone and 15 parts "TONE P-300" (10,000 molecular weight) polycaprolactone were placed in an open vessel and heated in an oven at 80° C. until both components were fluid. The vessel was transferred to an 80° C. water bath and the mixture stirred until homogeneous. The resultant blend was poured onto polyester sheeting atop a horizontal platform. A second polyester sheet was placed atop the molten mass. A roller was used to form the blend into sheets of approximately 2-4 mm thickness. The sheets were transparent while warm and became opaque when cooled under a stream of cold water.

Using a similar procedure a control composition (containing 100% "TONE P-767" polycaprolactone) and twenty additional high molecular weight/low molecular weight polycaprolactone blends were prepared. Set out below in TABLE I are the types, amounts and molecular weights of the high molecular weight ("HMW") and low moleculer weight ("LMW") polycaprolactones in each composition, and several physical properties for each composition. Warm state viscosity was measured at 65° C. using a rheometric dynamic analyzer (Rheometrics Inc.) operating at 20% maximum strain and a 1 radian/second strain rate. Cool state storage modulus was measured at 30° C. on the rheometric dynamic analyzer, operated at 1.4% maximum strain and a 10 radian/second strain rate.

Dimensional stability was evaluated using a modified version of American Dental Association (ADA) Test Specification No. 19 (J.A.D.A., 94, 733 (1977)). Each molding composition was heated to 80° C. until molten and poured onto the ruled die prescribed in the Test Specification. A transparent rigid plate was placed atop the molten composition, and secured to the ruled die with a clamp. The molten composition was allowed to cool for 5 minutes at room temperature. The clamp and solidified molding composition were removed from the die. The resulting model was stored at 23±1° C. and 50±5% relative humidity for 24 hours. Dimensional stability was determined by comparing the distances between the ruled lines on the model and on the ruled die using an optical comparator.

Compression set was evaluated using a modified version of ADA Test Specification No. 19. Each molding composition was heated to 80° C. until molten, and transferred to the standard compression set cylindrical mold prescribed in the Test Specification. The mold endplates were clamped into place and the mold and its contents cooled in a 22° C. water bath for 5 minutes. The resulting solidified model was removed from the mold. Each model was axially compressed 1.0 mm for 30 seconds using a metered screw clamp. The clamp was released and a measurement of permanent deformation recorded one minute later. The percentage change in cylinder height was calculated to determine compression set.

Strain-in-compression was evaluated using a modified version of ADA Test Specification No. 19. Cylindrical models were prepared according to the compression set test described above. The cylinder height was measured, a 1.125 kg mass was placed atop the cylinder, and a second height measurement was recorded thirty seconds later. The percentage change in cylinder height was calculated to determine strain-in-compression.

Inlay accuracy was evaluated by heating each molding composition to 65° C., and using the resulting molten compositions to make an impression of a Class II MOD preparation on the lower left first molar of a "TYPODONT" model (Columbia Dentoform Corp.). The molten compositions were applied evenly to the second premolar, the prepared first molar and the second molar, and pressed into place using finger pressure while in the transparent, molten state. Each composition was cooled for 60 seconds using a stream of cold water and then removed from the TYPODONT model yielding a completed opaque impression. A standard gypsum "stone" model was poured in each impression. The hardened stone model was easily removed from the impression by slightly warming the impression to about 60° C. in a water bath. An inlay was fabricated on each stone model in the following manner. A thin film of room-temperature vulcanizing silicone ("IMPRINT", 3M) was applied to the MOD preparation on the stone model and allowed to cure. Light curable restorative material ("SILUX PLUS", 3M) was tamped into the MOD preparation and shaped and carved to provide proper fit and anatomy. The restorative material was irradiated with a visible light curing lamp ("VISILUX 2", 3M) for 60 seconds. The resulting photohardened inlays were removed from the stone model and evaluated for overall fit on the original TYPODONT model preparation. Inlays were rated by two evaluators as providing excellent ("++"), acceptable ("+"), or unacceptable ("−") fit.

TABLE I

| Run No. | HMW PCL Type | HMW PCL Parts | LMW PCL Type | LMW PCL Parts | Viscosity, 65° C., Kilopoise | Modulus, 30° C., dyne/cm$^2$ × 10$^8$ | Dimensional stability, % shrinkage | Compression set, % | Strain in compression, % | Inlay fit |
|---|---|---|---|---|---|---|---|---|---|---|
| 1 | P-767[1] | 100 | None | 0 | 84.0 | 8.2 | 0.70 | 0.98 | 0.38 | — |
| 2 | " | 85 | P-300[2] | 15 | 21.6 | 13.1 | 0.86 | 1.03 | 0.25 | — |
| 3 | " | 70 | " | 30 | 19.3 | 12.4 | 0.87 | 1.25 | 0.45 | — |
| 4 | " | 55 | " | 45 | 7.8 | 7.2 | 0.62 | 1.05 | 0.30 | ++ |
| 5 | " | 85 | 0260[3] | 15 | 43.3 | NM[4] | 0.89 | 0.95 | 0.33 | + |
| 6 | " | 70 | " | 30 | 8.9 | 14.5 | 0.93 | 0.95 | 0.30 | ++ |
| 7 | " | 55 | " | 45 | 7.2 | NM[4] | 0.83 | 1.10 | 0.30 | + |
| 8 | " | 85 | 0240[5] | 15 | 17.6 | 13.0 | 0.96 | 1.03 | 0.35 | + |

TABLE I-continued

| Run No. | HMW PCL Type | HMW PCL Parts | LMW PCL Type | LMW PCL Parts | Viscosity, 65° C., Kilopoise | Modulus, 30° C., dyne/cm$^2$ × 10$^8$ | Dimensional stability, % shrinkage | Compression set, % | Strain in compression, % | Inlay fit |
|---|---|---|---|---|---|---|---|---|---|---|
| 9  | " | 70 | "     | 30 | 10.2 | 14.5 | 0.88 | 1.00 | 0.43 | + |
| 10 | " | 55 | "     | 45 | 5.3  | 13.3 | 0.95 | 0.93 | 0.45 | ++ |
| 11 | " | 85 | 2240[6] | 15 | 8.0  | 12.4 | 0.87 | 0.85 | 0.75 | ++ |
| 12 | " | 70 | "     | 30 | 13.1 | 12.4 | 0.71 | 1.03 | 0.38 | − |
| 13 | " | 55 | "     | 45 | 2.6  | 9.3  | 0.72 | 0.98 | 0.35 | ++ |
| 14 | " | 85 | 0230[7] | 15 | 33.7 | 11.3 | 0.91 | 0.83 | 0.43 | + |
| 15 | " | 70 | "     | 30 | 16.3 | 9.0  | 0.78 | 0.90 | 0.40 | +/++ |
| 16 | " | 55 | "     | 45 | 6.2  | 11.3 | 0.58 | 0.78 | 0.45 | − |
| 17 | " | 85 | 0305[8] | 15 | 11.6 | 7.9  | 0.71 | 0.75 | 0.48 | ++ |
| 18 | " | 70 | "     | 30 | 19.7 | 6.2  | 0.77 | 0.80 | 0.55 | ++ |
| 19 | " | 55 | "     | 45 | 7.3  | 3.1  | 0.74 | 0.83 | 0.48 | ++ |
| 20 | " | 85 | 0200[9] | 15 | 34.7 | 10.9 | 0.82 | 0.90 | 0.30 | − |
| 21 | " | 70 | "     | 30 | 7.9  | 7.5  | 0.75 | 0.98 | 0.78 | +/++ |
| 22 | " | 55 | "     | 45 | 84.0 | 4.0  | 0.66 | 0.98 | 0.63 | +/++ |

[1]"TONE P767" 40,000 molecular weight polycaprolactone (Union Carbide Corp.).
[2]"TONE P-300" 10,000 molecular weight polycaprolactone (Union Carbide Corp.).
[3]"TONE 0260" 3,000 molecular weight polycaprolactone (Union Carbide Corp.).
[4]"NM" = Not measured.
[5]"TONE 0240" 2,000 molecular weight polycaprolactone (Union Carbide Corp.).
[6]"TONE 2240" 2,000 molecular weight polycaprolactone (Union Carbide Corp.).
[7]"TONE 0230" 1,250 molecular weight polycaprolactone (Union Carbide Corp.).
[8]"TONE 0305" 540 molecular weight polycaprolactone (Union Carbide Corp.).
[9]"TONE 0200" 530 molecular weight polycaprolactone (Union Carbide Corp.).

The above data illustrates the extent to which a reduction in warm state viscosity and an increase in cool state modulus can be attained, by blending low molecular weight polycaprolactone with high molecular weight polycaprolactone. The data is further illustrated in FIGS. 1 and 2. FIG. 1 shows an unsmoothed plot of viscosity at 65° C. vs. percent low molecular weight polycaprolactone for Runs 1-22 of TABLE I. Curves A through G connect the data points for blends containing the "TONE" low molecular weight polycaprolactones "0260", "0230", "0200", "P-300", "0240", "0305", and "2240", respectively. As shown in FIG. 1, even relatively small additions of low molecular weight polycaprolactone provide a substantial viscosity reduction. For example, addition of only 15% "TONE P-300" (10,000 molecular weight) polycaprolactone provides a 74% viscosity reduction. The resulting blend was a free-flowing, homogeneous, transparent pourable liquid at 65° C., which readily flowed into fissures and other interstices in a mold.

Figure 2:
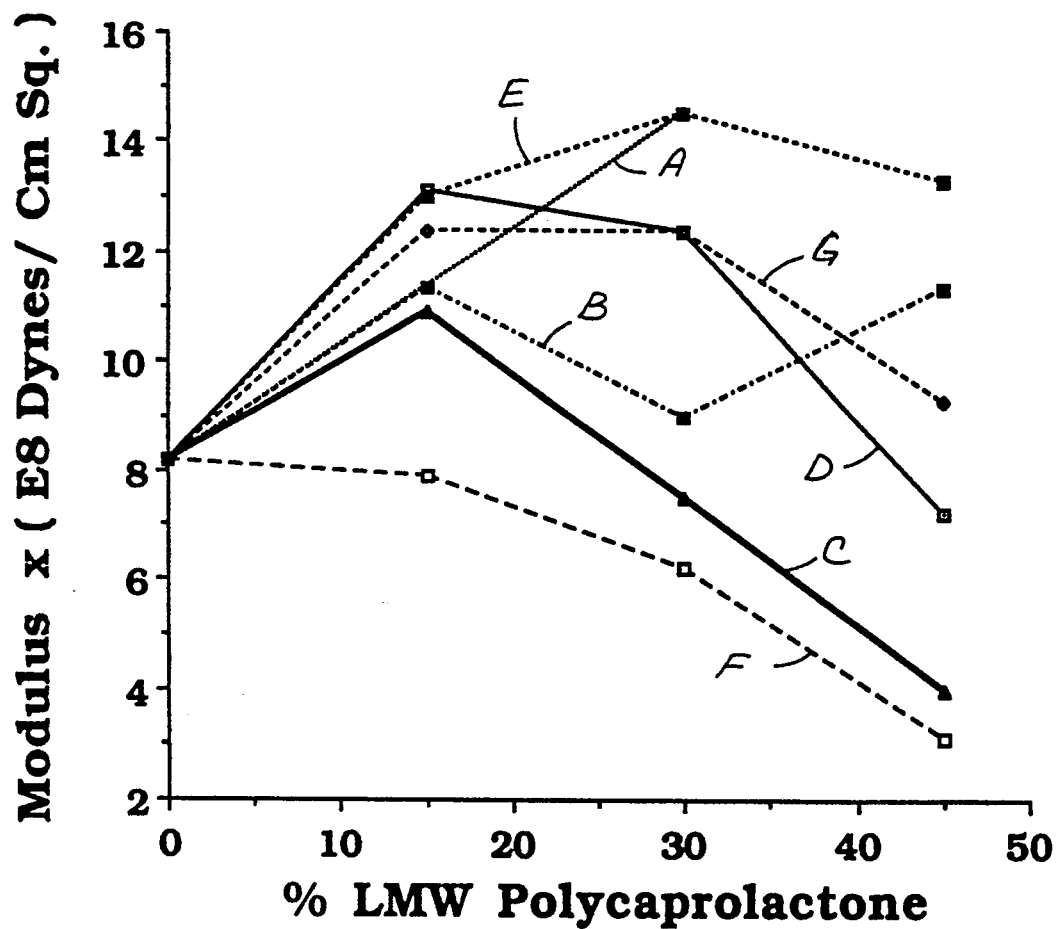
FIG. 2 is a plot of storage modulus vs. percent low molecular weight polycaprolactone for the compositions of Runs 1-22 of EXAMPLE 1.

Referring now to FIG. 2, an unsmoothed plot of modulus at 30° C. vs. percent low molecular weight polycaprolactone is shown for Runs 1-22 of TABLE I. The curves are labeled as in FIG. 1. With the possible exception of the blends containing "TONE 0305" (540 molecular weight) polycaprolactone (whose modulus was not measured in the region between 0 and 15% low molecular weight polycaprolactone), the remaining blends all exhibited increased modulus at appropriate low molecular weight polycaprolactone addition levels. This increase in modulus is manifested by reduced flexibility and greater handling strength in the cooled state. As shown in FIG. 2, even relatively small additions of low molecular weight polycaprolactone provide a substantial modulus increase. For example, addition of only 15% "TONE P-300" polycaprolactone provides a 60% modulus increased. The resulting blend formed a stiff, handleable opaque white sheet at 30° C.

Several of the molding compositions shown in TABLE I should meet the ADA's requirements for impressioning materials, and should permit the fabrication of excellent inlays and other dental prosthetic devices.

EXAMPLE 2

Figure 3:
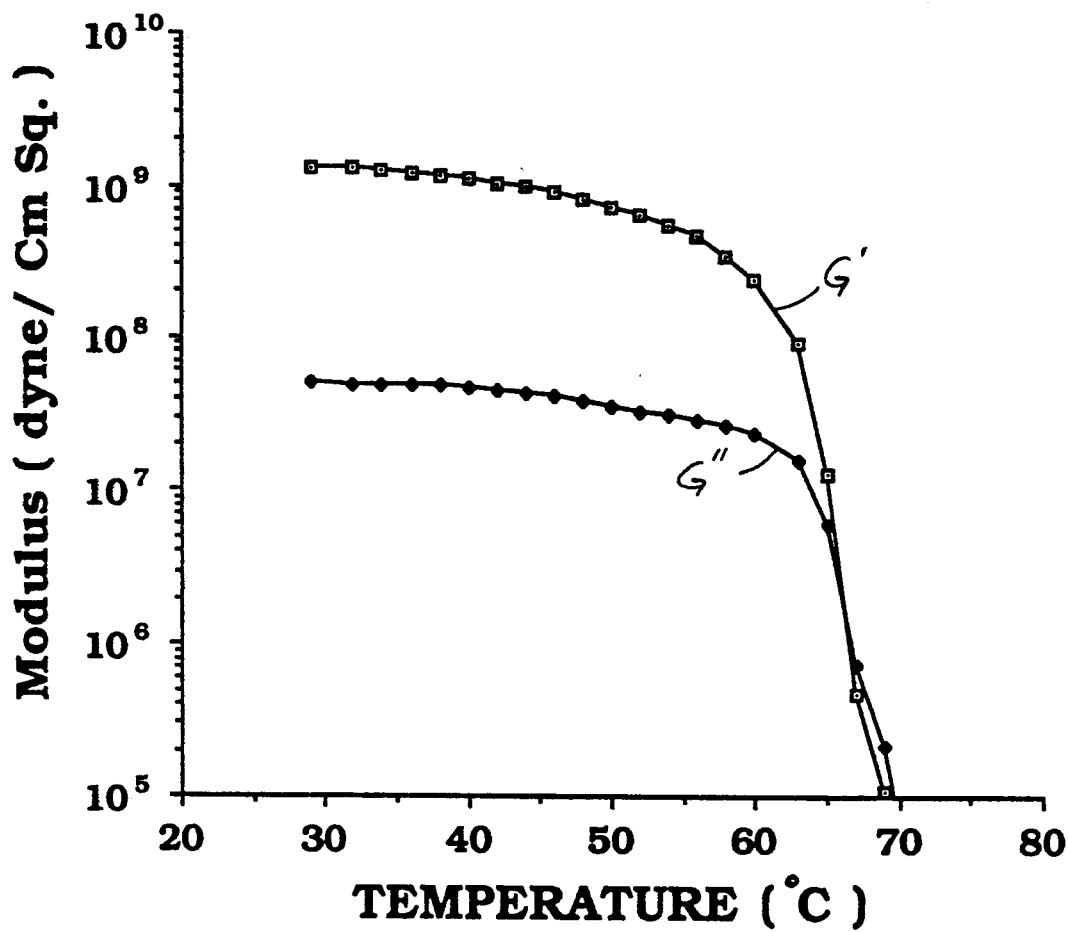
FIG. 3 is a plot of storage and loss moduli for the composition of Run 2 of EXAMPLE 1.

Rectangular 2.5×13×33 mm torsion bars were cast from the molding composition of Run 2 of EXAMPLE 1, and evaluated for storage and loss moduli (G, and G", respectively) using a rheometric dynamic analyzer operated at 1.4% maximum strain and a 10 radian/second strain rate. FIG. 3 contains a plot of the modulus measurements between 32° C. and 70° C. The data shows that the composition had a sharp melting point at temperatures that would be acceptable in the mouth. At body temperature (about 38° C.), the molding composition exhibits solidity, usefully high modulus, and desirably low plasticity.

Although this invention has been described using certain illustrative examples, it should be understood that the invention is not limited to the specific exemplary embodiments shown in this specification.

We claim:

1. A method for making an impression of dental tissue, comprising the step of enveloping the tissue with a molten or softened molding composition comprising a blend of high molecular weight and low molecular weight polycaprolactones.

2. A method according to claim 1, wherein the composition has a melting or softening temperature less than about 75° C., and is a solid at 38° C.

3. A method according to claim 2, wherein the composition has a melting or softening temperature less than about 65° C.

4. A method according to claim 1, wherein the composition is in the form of a warm arch-shaped tray that is placed into contact with the dental tissue.

5. A method according to claim 1, wherein the composition is in the form of an arch-shaped tray that is warmed above its melting or softening temperature, shaped intraorally to conform generally to the shape of the dental tissue, cooled to solidify the tray, filled with an elastomeric impression material, and reinserted in the mouth so that the elastomeric impression material will make an accurate replica of the shape of the dental tissue.

6. A method according to claim 1, wherein the composition is used to prepare a bite registration impression of opposing dentition.

7. A method according to claim 1, wherein the composition comprises at least one layer of a multi-layer thermoplastic molding composition.

* * * * *

UNITED STATES PATENT AND TRADEMARK OFFICE
CERTIFICATE OF CORRECTION

PATENT NO. : 5,066,231
DATED : November 19, 1991
INVENTOR(S) : Oxman et al.

It is certified that error appears in the above-identified patent and that said Letters Patent is hereby corrected as shown below:

Col. 1, line 17, "moldirg" should be --molding--.

Col. 2, line 16, "observed" should be --observed.--.

Col. 3, line 24, "TONE P-:00" should be --TONE P-300--.

Col. 4, line 3, "$pecialties" should be --Specialties--.

Col. 4, line 44, "as," should be --as--.

Col. 5, line 4, "mamacroscopic" should be --macroscopic--.

Col. 5, line 22, "pclycaprolactone" should be polycaprolactone--.

Col. 6, line 20, "cooled" should be --cooled.--.

Col. 6, line 56, "tructure" should be --structure--.

Col. 10, line 25, "(G, and G"," should be --(G' and G",--.

Signed and Sealed this

First Day of March, 1994

Attest:

BRUCE LEHMAN

Attesting Officer      Commissioner of Patents and Trademarks